United States Patent [19]

Liprie

[11] Patent Number: 4,819,618

[45] Date of Patent: Apr. 11, 1989

[54] IRIDIUM/PLATINUM IMPLANT, METHOD OF ENCAPSULATION, AND METHOD OF IMPLANTATION

[76] Inventor: Sam F. Liprie, P.O. Box 834, Lake Charles, La. 70602-0834

[21] Appl. No.: 24,663

[22] Filed: Mar. 11, 1987

Related U.S. Application Data

[63] Continuation-in-part of Ser. No. 897,544, Aug. 18, 1986, which is a continuation-in-part of Ser. No. 778,410, Sep. 20, 1985, abandoned.

[51] Int. Cl.$^4$ .............................................. A61N 5/00
[52] U.S. Cl. ...................................... 600/7; 128/772; 228/138; 600/3
[58] Field of Search ................ 128/1.1, 1.2, 656–658, 128/772; 604/282; 228/135, 138

[56] References Cited

U.S. PATENT DOCUMENTS

| | | | |
|---|---|---|---|
| 2,546,761 | 3/1957 | Loftus | 128/1.2 |
| 2,749,086 | 7/1973 | Kline et al. | 128/772 |
| 2,798,164 | 7/1957 | Untermyer | 128/1.2 |
| 3,060,924 | 10/1962 | Rush | 128/1.2 |
| 3,485,234 | 12/1969 | Stevens | 604/282 |
| 3,612,058 | 10/1971 | Ackerman | 128/772 |
| 3,674,006 | 7/1972 | Holmer | 128/1.2 |
| 3,924,632 | 11/1975 | Cook | 604/282 |
| 4,096,862 | 6/1978 | DeLuca | 128/1.2 |
| 4,425,919 | 1/1984 | Alston et al. | 604/282 |
| 4,538,622 | 9/1985 | Samson et al. | 128/772 |
| 4,554,929 | 11/1985 | Samson et al. | 128/772 |

FOREIGN PATENT DOCUMENTS 857992 1/1961 United Kingdom ............... 128/1.2

Primary Examiner—Francis Jaworski
Assistant Examiner—John C. Hanley
Attorney, Agent, or Firm—Pravel, Gambrell, Hewitt, Kimball & Krieger

[57] ABSTRACT

A IR-192 platinum wire implant includes a core area 0.1 mm in diameter, comprised of 25 percent iridium and 75 percent platinum. This core area is encased in a 100 percent platinum sheath of 0.15 mm thickness in cross-section and 0.075 mm thickness at its end portions. Therefore, the entire implant insert is 0.4 mm in diameter. Further, the iridium/platinum composite implant includes means for allowing it to be cut to any length desired so that cutting of the composite metal through cross-section would effectively squeeze the 0.15 mm sheath coating around the end portion of the iridium/-platinum core and effectively achieve the 0.075 mm thickness at the end portion, thus sealing the end portion of the implant. There would further be provided a method for achieving the cutting of the composite implants to various pre-determined lengths and maintaining the sealed end portions upon completion of the cut. There is further provided the step of arc welding a flexible housing to an inner stainless steel guide member to which the implant is bonded in order to provide a continuous flexible guide for the implant.

20 Claims, 5 Drawing Sheets

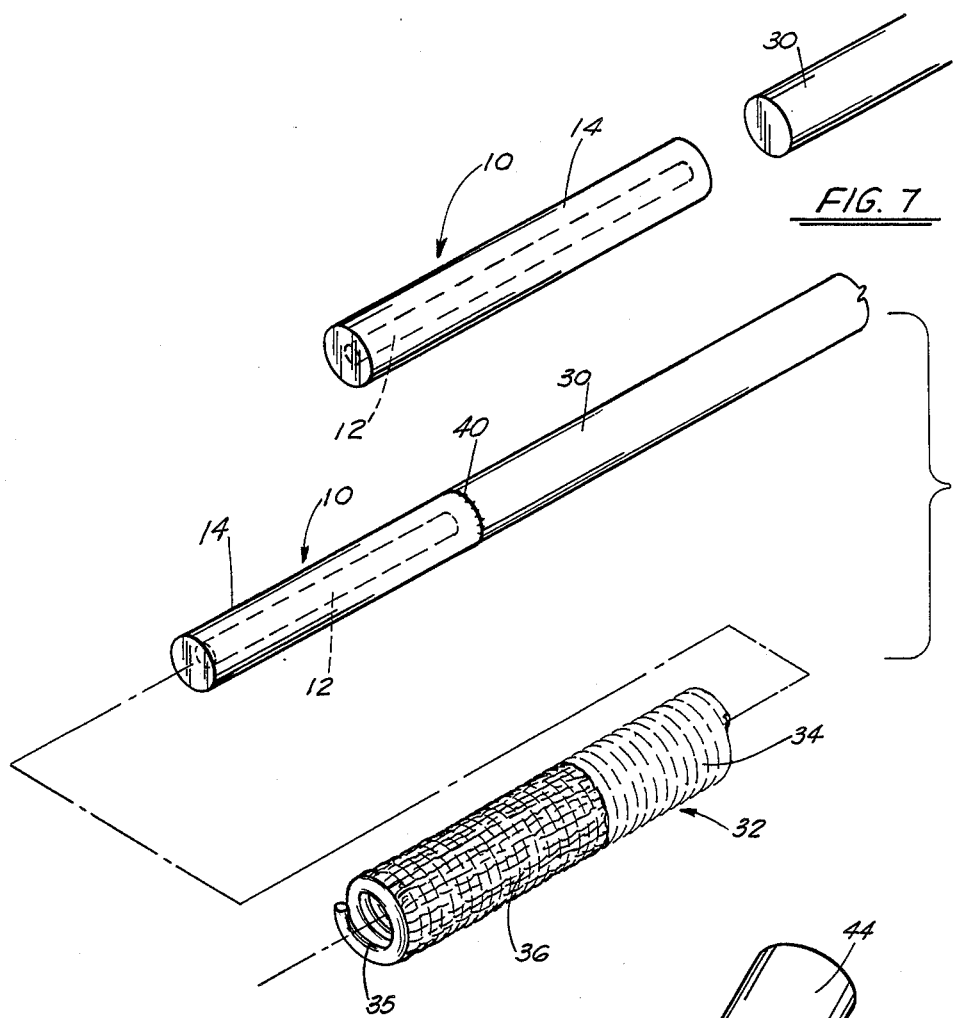
FIG. 7
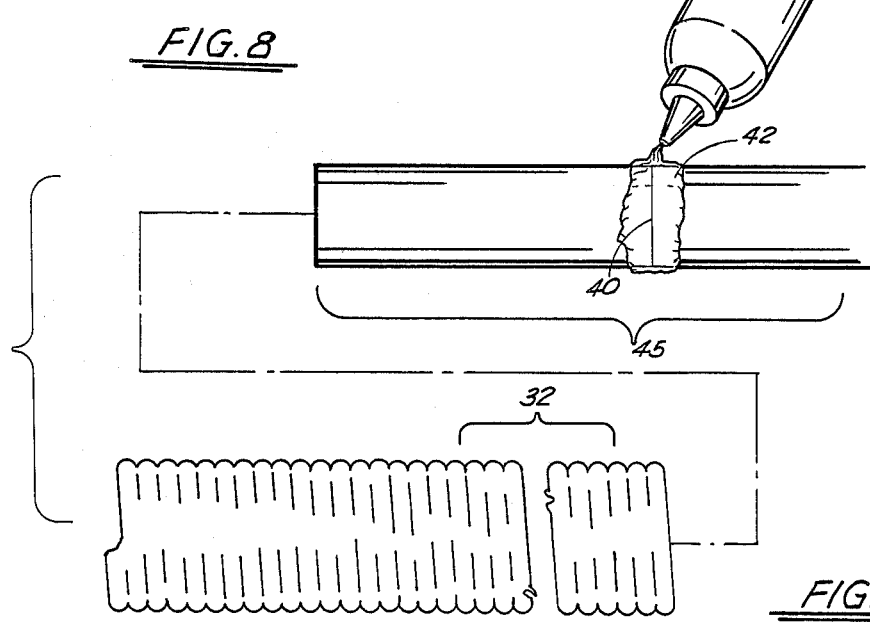
FIG. 8
FIG. 9

IRIDIUM/PLATINUM IMPLANT, METHOD OF ENCAPSULATION, AND METHOD OF IMPLANTATION

This is a Continuation-in-Part of U.S. patent application, Ser. No. 897,544, filed Aug. 18, 1986, entitled "Iridium/Platinum Implant, Method Of Encapsulation, And Method Of Implantation", which was a Continuation-in-Part of U.S. patent application, Ser. No. 778,410, filed Sept. 20, 1985, now abandoned, both by the same inventor.

BACKGROUND OF THE INVENTION

1. Field of the Invention

The present invention relates to body implants. More particularly, the present invention relates to a radioactive filament comprising an iridium/platinum alloy core and a pure platinum sheath, which can be cut to predetermined lengths without unwanted leakage of the radioactivity, and a method of treating the implant for insertion into certain areas of the body for treatment of body tumors.

2. General Background

In the area of medicine that addresses the treatment of tumors in the body, one such method of treatment is the insertion of implants into the tumor which have been previously radioactive and that emit radioactivity in order to shrink or "kill" a tumor, referred to in the field as Interstitial Brachytherapy.

The procedure involved in this type of therapy would be to insert the radioactive implant through a plastic catheter that has been previously inserted into the tumor from the outside of the body. Once the implant is in the tumor, then the radioactivity emitted by the implant would hopefully destroy the cancerous cells around it. However, there are shortcomings to this technique in utilizing the particular type of implants presently on the market. One of the most common type of implants is the IR-192 seed implants which are iridium/platinum seeds spaced inside a nylon or plastic tube for insertion into the cancer. The IR-192 seeds are 3 mm in length and are commonly spaced 7 mm apart so that there exists a known standard distance of one (1) centimeter between the center of each seed. The IR-192 core contained in each of the seeds cannot be exposed at any of their surfaces to the exterior since the radioactivity would bleed from the iridium core and cause damage. Therefore, it is absolutely necessary that the iridium platinum core be in a sheath of platinum at all times. Since there is spacing between the seeds of the nylon or plastic tubing, when inserted into the body of a tumor, the portions of tubing which are not housing the iridium or IR-192 seeds are not emitting radioactivity, and thus the tumor is only being "partially" treated. Likewise, in the cases where the IR-192 seed must be inserted into an area of the body which is not straight, for example an endobronchial implant, tongue implants, tonsil implants, and many other areas that are not readily accessible for treatment, the catheter must be first put in place by traversing a difficult path composed of many turns, tight angles and curves in order to get to the area needing treatment. The IR-192 implant that is to be contained within the catheter can follow only after the tedious task of insertion of the catheters has been accomplished. Since there are spaces between the seeds, many times the nylon or plastic tubing will bend and kink as one attempts to make it move through the curvature of the catheter that leads to the area to be treated, and it becomes impossible to move any further.

Likewise, in addition to the IR-192 seeds, there are some products on the market that are being sold which are pre-determined lengths of encapsulated IR-192 wires. The IR-192 wire implant does have the significant advantage over the IR-192 seed due to the fact that it is a continuous treatment surface and does not contain gaps. However, its shortcomings is that it must be sold only in pre-determined lengths, since any attempt to cut the wire to more precise lengths would cause a leakage in the wire as it would not be self sealing and would thus be unacceptable for use.

Under present guidelines, a radioactive sealed source, whether it is in the form of a wire or seed, has to be leak tested at least every six months. Since the wire is sold in pre-determined lengths and is encapsulated, it is not leaking and is sold as such. Almost every body tumor to be treated is different in size and shape; and, in most cases, more than likely, the wire would have to be cut in order to precisely fit the tumor or cancer area. In the case of IR-192 wire, as was stated earlier, this cannot be done; and therefore, the tumor will not be properly covered.

Further, in order to get the implant (a radioactive part), into the upper lobe for an endobronchial implant, it is necessary that the IR-192 wire be placed into a 0.035" or 0.038" guidewire housing for maneuvering the implant around several curves, etc., within the body in order to reach the upper lobe. In this procedure, the implant is mounted inside a 0.035" or 0.038" guidewire and inserted through a special balloon catheter that is placed through the nasal passage and anchored into place inside the area needing treatment. The problem associated with passing the implant through the balloon catheter is that there is usually one or two sharp angles or curves along this route, especially when inserting into the upper lobe. Previously, in these areas where the curves are difficult, the pressure inserted in attempting to maneuver the implant through the curves would actually cause a kink where the implant and core inside the guidewire meet, allowing no further advancement of IR-192 wire implant. The area needing treatment could not always be reached. Therefore, there is a need to join the iridium wire to the stainless steel wire inside the guide-wire, so that no kinking will occur, and the implant can be inserted into the area that needs to be treated.

Further, in the area of brain implants, if the IR-192 wire implant would not join to a stainless steel wire of approximately the same outside diameter, the IR-192 wire would have to be mounted inside a small nylon catheter. For example, the nylon catheter presently used has an outer diameter of 0.85 mm. The wire alone is 0.4 mm. A brain implant procedure entails drilling a hole inside the brain for placement of the IR-192 wire. The catheter is slipped inside this hole. If the nylon catheter is used, a hole twice as large as what is needed inside the brain will have to be drilled. By joining the IR-192 wire to a stainless steel wire, one is able to lower it through a hole with the outside diameter smaller than 0.5 mm, since the diameter of the IR-192 wire is only 0.4 mm. Because of the high risk involved in drilling into the brain, the smaller hole is obviously a greater advantage.

U.S. patent application, Ser. No. 778,410, entitled "Iridium/Platinum Implant And Method Of Encapsulation", by the same inventor, now abandoned, disclosed the method by which an IR-192 platinum wire implant, having a core area comprised of 25% iridium and 75% platinum, could be cut to a proper length for use to treat tumors, whereby the method of cutting assured that the end portions of the implant were automatically sealed around the iridium/platinum core so that no radiative leakage would occur.

U.S. patent application, Ser. No. 897,544, entitled "Iridium/Platinum Implant, Method Of Encapsulation, And Method Of Implantation", also by the same inventor, claimed an improvement in the parent application, in that the method of preparing and implanting a radioactive implant into the body included a guide member that was secured to the implant for guiding the implant to the portion of the body, including a flexible housing for positioning the implant guide member within the housing. There was applied a compound to the exterior of the housing for achieving a bond between the exterior housing, the implant and guide member, so that the guide member and the implant could be maneuvered to an area of the body and kinking between the implant member and the guide member would be avoided.

There are several patents which were issued in the field, the most pertinent being as follows:

| Patent No: | Inventor: | Invention: |
| --- | --- | --- |
| 2,429,438 | Wappler | "Tubular Bodies Such As Radium Seeds" |
| 2,322,902 | Wappler | "Apparatus For Making Tubular Bodies" |
| 3,438,365 | Packer, et al | "Radioactive Seed Container Xenon Gas For Medical Treatment" |

SUMMARY OF THE PRESENT INVENTION

The wire implant of the present invention solves the shortcomings in the art in a simple and straightforward manner. What is provided is a IR-192 platinum wire implant which includes a core area 0.1 mm in diameter, comprised of 25 percent iridium and 75 percent platinum. This core area is encased in a 100 percent platinum sheath of 0.15 mm thickness in cross-section and 0.075 mm thickness at its end portions. Therefore, the entire implant insert is 0.4 mm in diameter. Further, the iridium/platinum composite implant includes means for allowing it to be cut to any length desired so that cutting of the composite metal through cross-section would effectively squeeze the 0.15 mm sheath coating around the end portion of the iridium/platinum core and effectively achieve the 0.075 mm thickness at the end portion, thus sealing the end portion of the implant. There would further be provided a method for achieving the cutting of the composite implants to various pre-determined lengths and maintaining the sealed end portions upon completion of the cut.

The method of preparing the IR-192 implant for insertion into troublesome areas in the body, through the use of a guidewire, which incorporates a stainless steel inner core and a hollow outer core, includes adhering the end of the IR-192 implant wire to a first end of a stainless steel wire via arc welding or the like means of attachment. Further, the attachment point is then treated and encased in a compound of cyanoacrylate ester or similar type of quick drying compound, for preventing radioactive leakage from the IR-192/steel attachment point. Further, the point of attachment is then inserted into the guide sheath, a sheath having an inner core of stainless steel tightly wound metal and an outer layer polytetrafluoroethylene (PTFE - sold under the trademark Teflon). The PTFE outer coating is removed from the guidewire sheath at that point that the attachment point lies within the guidewire sheath. Following the placing of the additional coating of the cyanoacrylate ester at the junction of the two wires, with the inner core wire mounted flush inside the exterior guidewire, two electro-clips are used to touch various areas along the guidewire, so that in every instance that the two electro-clips touch, there is created a arc weld between the wires which results in the inner core being firmly welded to the outer guidewire encompassing it. As an additional safeguard in strengthening the wire, an additional layer of cyanoacrylate ester is incorporated through the outer coating guidewire to penetrate to the inner core of the junction where the IR-192 wire and stainless steel core were joined. Following this procedure, the guidewire and the stainless steel wire, having been arc welded at various points along their length, are then able to be maneuvered within the balloon catheter through the troublesome zones where kinking, which would normally occur, is prevented by the improved guide wire/stainless steel wire arc weld connections.

Therefore, it is an object of the present invention to provide the iridium/platinum composite implant to predetermined lengths for insertion into body tumors;

It is a principal object of the present invention to provide an iridium/platinum composite implant having an iridium/platinum core in a pure platinum sheath;

It is still a further object of the present invention to provide a radioactive implant for body tumors which has a 0.1 mm iridium/platinum core and a 0.15 mm platinum sheath with a 0.075 mm end thickness of the sheath;

It is still a further object of the present invention to provide a radioactive iridium/platinum composite implant for treatment of body tumors which can be cut and sealed against radioactive leakage simultaneously;

It is still a further object of the present invention to provide a method for cutting pre-determined lengths of iridium/platinum composite of body tumor implant which includes cutting the implant to a predetermined length and simultaneously sealing the end portions, as it is cut, against leakage of radioactivity.

It is a further principal object of the present invention to provide a method for preparing the iridium/platinum composite implant for movement into certain areas of the body;

It is still a further object of the present invention to provide a method for adhering the iridium/platinum composite implant to a stainless steel wire, treating the point of contact, inserting the stainless steel wire implant into a guidewire sheath and arc welding the guide sheath to the stainless steel wire at points along their length, to strengthen the connection between the guidewire and the stainless steel wire so that the IR-192 implant can be moved into troublesome areas of the body without kinking along the length of the implant.

BRIEF DESCRIPTION OF THE DRAWINGS

A better understanding of the invention can be had when the detailed description of a preferred embodiment set forth below is considered in conjunction with the drawings, in which:

FIG. 7 is a view of the implant and stainless steel wire of the present invention;

FIG. 8 is a overall view of the implant attached to the stainless steel wire and being positioned within the guidewire sheath;

FIG. 9 is an overall view of the IR-192 wire/stainless steel guidewire component being inserted into the guidewire sheath after being treated with a gluing compound;

DETAILED DESCRIPTION OF THE PREFERRED EMBODIMENT

Figure 1:
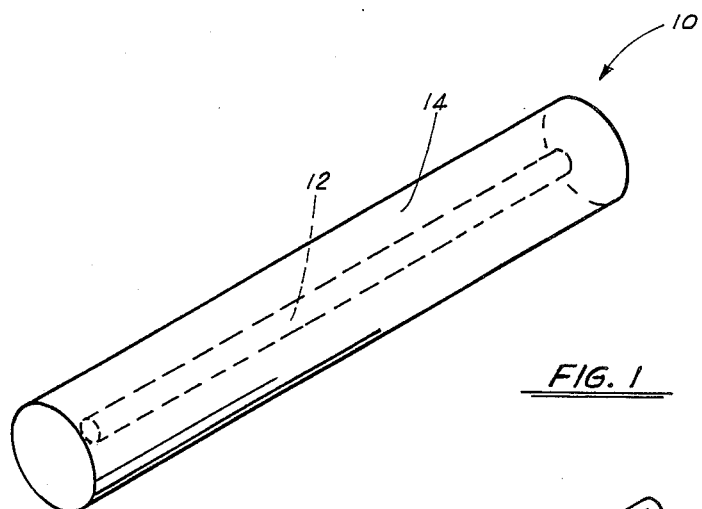
FIG. 1 is an overall perspective view of the preferred embodiment of the implant of the present invention.
Figure 2:
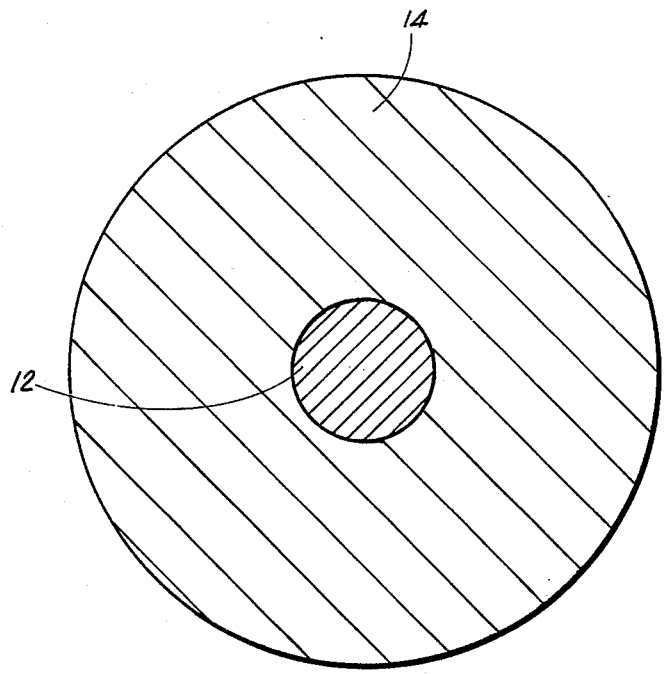
FIG. 2 is a cross sectional view of the preferred embodiment of the implant of the present invention.
Figure 3:
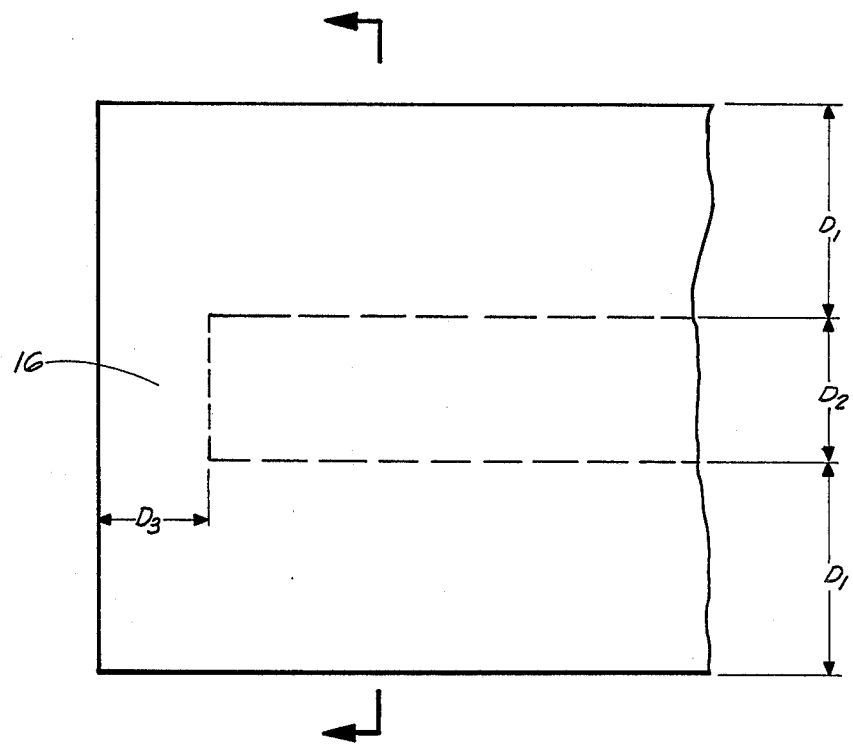
FIG. 3 is a partial side view of the preferred embodiment of the implant of the present invention.

FIGS. 1–3 illustrate the preferred embodiment of the apparatus of the present invention indicated by the numeral 10. Iridium/Platinum composite implant 10 (hereinafter referred to as implant 10), as seen in FIGS. 1 through 3, comprises an inner Iridium/Platinum alloy core member 12 housed in a pure platinum sheath 14. In the preferred embodiment, the Iridium/Platinum core member 12 would comprise 25 percent pure iridium and 75 percent pure platinum in the alloy composite, and would be preferably 0.1 mm in diameter along diameter D2 as seen in FIG. 3. Likewise, pure platinum sheath 14 would comprise 100 percent pure platinum and would have an inside diameter equal to D2, and an outside diameter equal to D1 plus D2 plus D1. Likewise, the preferred embodiment Iridium/Platinum core member 12 would be encased by the pure platinum sheath 14 at its end portions of a thickness of 0.075 mm, as illustrated, indicated as D3 also in FIG. 3.

It is important to note that, at this point, the thickness D1 is crucial in the present invention, as would be illustrated further in the specification, and undertaking the method of cutting the implant 10 to a desired length, the thickness D1 of the pure platinum sheath 14 surrounding the core member 12, that thickness being preferably 0.15 mm, assures the sealing of the end portion 16 as illustrated by thickness D3 also in FIG. 3. This sealing of the end portion is absolutely crucial, since it would prevent any leakage of radioactivity from the cut implant, a problem which now plagues the industry.

Figure 4:
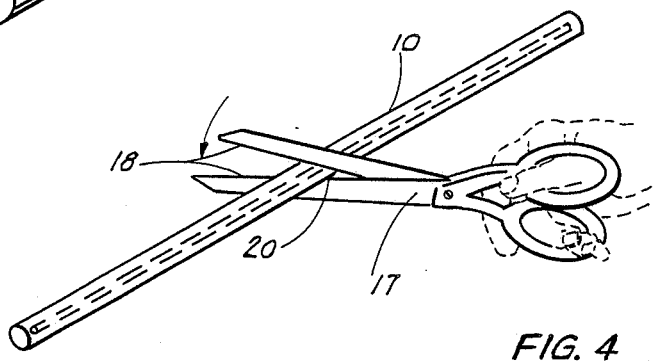
FIG. 4 is an overall view of the method of cutting the implant of the preferred embodiment of the present invention.
Figure 5:
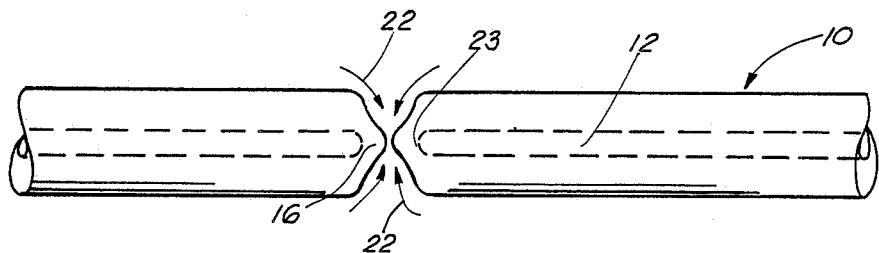
FIG. 5 is a side view illustrating the cut implant of the preferred embodiment of the present invention.

FIGS. 4 and 5 illustrate the method of cutting a length of implant 10, as will be discussed further. The Iridium/Platinum composite implant 10 comprising the iridium core member 12 and platinum sheath 14 could be provided in any length, preferably as a continuous length on a spool or the like. After one has determined a particular length required for a particular body tumor in question, as illustrated in FIG. 4, one would simply utilize preferably a pair of scissors 12 having dulled cutting edges 18 on each blade thereof. Upon determining where along the length of the implant 10 a cut would be made, the scissors would be closed to pinch off the implant wire at point 20. This pinching off the wire at point 20 would, in effect, as seen in FIG. 5, cause the wall of sheath 14 to be squeezed in the direction of ARROWS 22 as seen in FIG. 5, by blades 18, and in effect be squeezed over the cut ends 23 of core member 12 as seen in the FIGURE. FIG. 5 represents the cut ends of the implant 10 following the cutting by scissors 17, with the requisite thickness of 0.075 mm of end portion 16. This, as was stated earlier, ensures that the core member 12 is encased in the platinum sheath along the end portion 16; and therefore, no radioactive leakage would occur.

Figure 6:
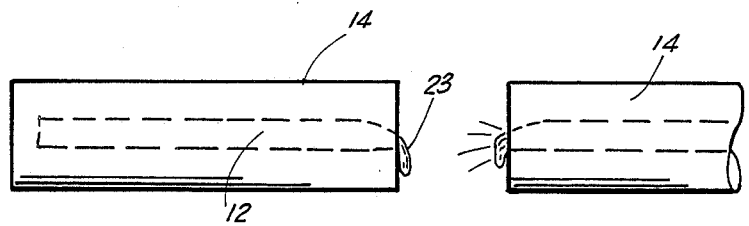
FIG. 6 is a view of the implant of the present invention that has undergone improper cutting.

FIG. 6 represents the length of filament which may have been improperly cut, i.e., without allowing the platinum wall to seal the end portions of the platinum wall 14, and to seal the end portion 23 of core member 12; and, therefore, core member 12 would be exposed to the outside, and would have radioactive leakage. This is a very undesirable situation and is avoided at all costs. For assuring that the end portion 16 of platinum wall 14 has been properly sealed through the cutting process, it may be desirable that the cut end be dipped and coated into a small quantity of quick-drying adhesive substance of the type marked as "super glue", or some similar such product and be allowed to completely dry. This hardened layer helps to form a firm encapsulation around the end of the wire thus avoiding any possibility that the initial sealing process was not successful. Therefore, any possibility that the iridium core member 12 might be exposed to the outside is eliminated, and absolutely no leakage will occur.

Again, it should be noted that of particular importance in the design of this inventive implant which allows the dulled scissor blades 18 of scissors 17 to pinch off and seal the ends of the implant 10 in the process, is a factor that the platinum sheath 14 is of the requisite thickness, i.e., 0.15 mm. This particular thickness is great enough to allow and provide for the sealing off of the end portion during the cutting process, yet of the necessary thickness to continue to allow it to be slipped into the plastic catheter 50 for insert.

Therefore, the desirable features of this particular implant and method of cutting to effect the sealing of the end portions now allows this field of medical specialty to provide radioactive implants for body tumors at any desired length needed, following the determination of the shape of the tumor. This is unlike the present state of the art whereby wire must be sold in pre-determined lengths in order to overcome the problem of leakage should the wire be cut. In addition, the present invention allows the implant to be implanted into areas such as were cited earlier wherein a curvature of the implant is required. This particular implant, since it does have a continuous core member, can be bent very effectively and can be implanted into difficult areas which, in the past, have been unable to be effectively treated.

As was stated earlier, although a component of the present invention is the fact that an iridium/platinum composite implant is disclosed having an iridium core member 12 and platinum sheath 14, and a certain length of the implant can be achieved without leakage from the iridium core 12 by pinching off the wire at a point at the end of the implant, so that the wall of sheath 14 is squeezed over the ends of core member 12 therefore seal. However, in situations where this implant must be implanted into very difficult areas of the body, for example, the upper lobe of an endobronchial implant process, the implant must be placed within a guidewire moved into the area to be implanted for treatment. However, one of the problems encountered as stated earlier was the fact that as one reaches certain sharp "curves", along the route for getting into the upper lobe, the point of juncture between the iridium/platinum composite implant and the core inside the guidewire, is that a kink occurs at that point, and the implant can proceed no further.

Therefore, in this improved process in the present invention, one is able to achieve the implant in difficult areas as follows. As seen in FIGS. 7-11, iridium/platinum composite implant 10 (hereinafter referred to as "IR-192 Wire 10"), is illustrated having outer platinum sheath 14 and inner iridium core member 12. Further represented in FIG. 7 is the end portion of a wire member, internal stainless steel wire 30, which is part of the guidewire component, and a guide member 32 comprising inner stainless steel inner sheath 34, which is actually a tight wound wire member 35 which effectively serves as a continuous wire sheath surrounding stainless steel wire 30. Further, casing sheath 34 is an outer layer 36 of PTFE which serves as an outer most coating of the guide member 32. PTFE is a compound which is very biocompatible and is not rejected by the body when inserted thereinto.

Figure 12:
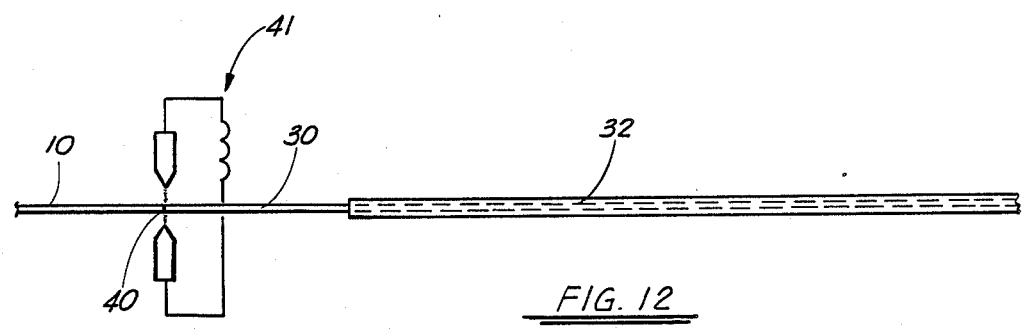
FIG. 12 illustrates an overall view of the improvement of the apparatus of the process of the present invention.

FIGS. 8 and 12 illustrate the means by which IR-192 wire 10 is attached to stainless steel wire 30. This means of attachment, in the preferred embodiment, is through the use of a process known as arc welding at point 40 by arc welding unit 41 (see FIG. 12), which is a standard arc welding unit having a pair of electrode clips that would make contact with implant 10 and wire 30 to form weld 40.

Figure 13:
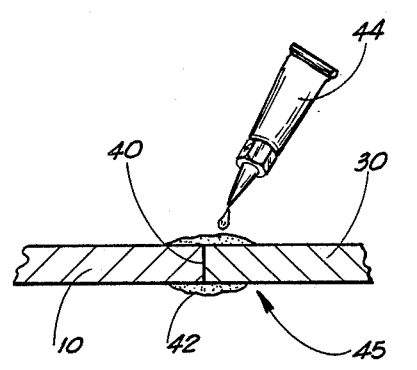
FIG. 13 represents an overall view of the initial adhesion between the stainless steel wire and the implant.

When this is achieved, there is a possibility that implant 10 may suffer radioactive leakage at juncture 40 from iridium core member 12. In order to overcome this possibility, it is further seen in FIGS. 9 and 13, there could further be included the step of coating the arc welded juncture 40 with gluing compound which is sold under the commercial name of "super-glue", and is actually a cyanoacrylate ester which is noted as item 42 in FIG. 9, the glue compound being contained in a container 44 for simply applying thereto as seen in the FIGURES. Upon application of the compound completely around the juncture 40, the compound solidifies very quickly, and any possibility of radioactive leakage from juncture 40 is precluded. For purposes of the type of compound used, it is possible that other compounds which could be utilized are epoxy, nail hardeners, or any type of quick drying compounds. However, in the preferred embodiment, the cyanoacrylate ester is the preferred compound.

Following the treatment of the juncture 40 with the compound 42, and allowing the compound to harden, the IR-192 wire 10/steel wire 30 component (hereinafter referred to as "COMPONENT 45"), as seen FIG. 9 is then inserted into sheath 32, as seen in FIGS. 8 and 9. It should be understood that the entire component 45 in sheath 32 is inserted into the body cavity, for example, in the case of the upper lobe of the bronchial area; therefore, it is preferred that the component 45 be held stationary within sheath 32 so that it may obtain further support from sheath 32 in the hard to maneuver curved areas of the cavity. Therefore, at this point in the process, following the insertion of the component 45 into sheath 32, this step in the process is seen in FIG. 10.

Figure 10:
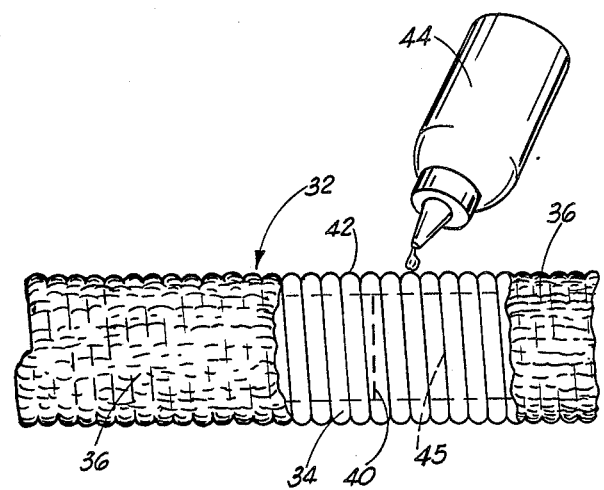
FIG. 10 is a view of the IR-192 wire/stainless steel guidewire component within the guidewire sheath being treated with a gluing component.
Figure 11:
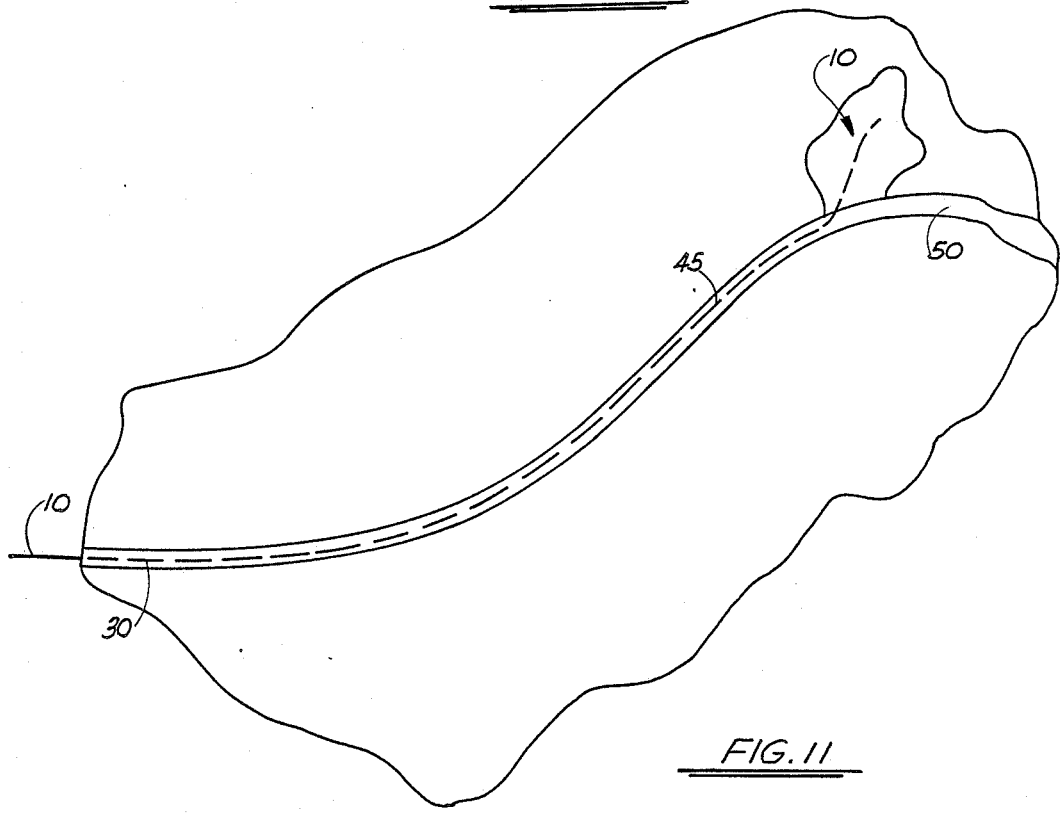
FIG. 11 is an overall view of the IR-192 wire/stainless steel wire component within the guidewire sheath being inserted into the body.
Figure 14:
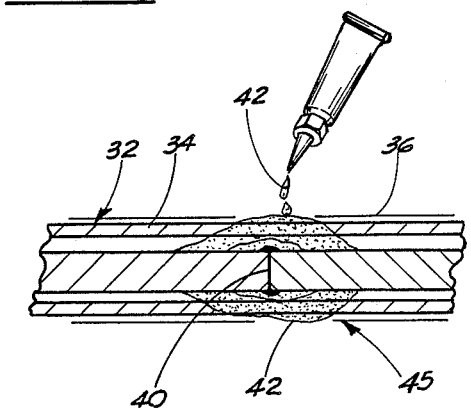
FIG. 14 illustrates an overall cross-sectional view of the guide wire/stainless steel wire, IR-192 implant secured within the guidewire.

Turning now to FIGS. 10 and 14, there is represented sheath 32 having outer most PTFE layer 36 and inner sheath member 34, with IR-192 wire/steel component 45 inserted there into. This step in the process at that point along the guidewire sheath 32 for juncture 40 is situated, the outer most PTFE layer 36 is removed from inner sheath 34 to completely expose sheath 34 at the point of juncture 40. At this time, a second application of glue compound 42 is applied to inner sheath 34, with glue 42 through flow spaces 47 in the tightly wound inner sheath 34 and therefore adhering the sheath 34 to the internal component 45 so that the component 45 is securely adhered within sheath 34 and cannot be maneuvered back and forth within sheath 34. Following this procedure and the hardening of the compound to form a composite formation at juncture 40, the guidewire 32 containing the component 45, as seen in FIG. 11, is then inserted into a catheter 50 and is tracked along to reach its end treatment point. It is through this treatment as was described in the specification, that the guidewire and IR-122 wire 10 is able to be maneuvered around difficult curves and corners without any kinking occurring and therefore a heretofore unsuccessful means of maneuvering to these difficult areas can now be achieved following this pretreatment process.

One of the novel features of this pretreatment process is the fact that the IR-192 wire 10 is permanently adhered to the inner steel wire 30 through arc welding or the like. However, there may be other means of attaching the stainless steel wire 30 to the IR-192 wire 10. However, both have certain limitations. The first option would be to use a very thin hollow piece of metal tube such as tube 34 that would actually slide over the stainless steel wire 30 and iridium wire 10. Utilizing a drop of the glue compound 42, inside the hollow sheath 34, is the junction of 10 and 30, so that the two wires were joined inside of the sheath or hollow tube, that is not using the process of arc welding. This would eliminate the kinking since it would strengthen the joint as it slides inside of the guidewire 32.

A second method would be to use a very thin piece of plastic or some type of heat-shrink material to join the stainless steel wire 30 and the IR-192 wire 10, heat shrinking at the joint. The limitations mentioned earlier are mainly the material covering the IR-192 wire/stainless steel wire component 45 would have to be extremely thin so that the two wires could be slipped inside of the guidewire. A larger guidewire cannot be used since this is the largest guidewire that would fit inside of the balloon catheter 50. A larger balloon catheter cannot be used since it would not fit in the smaller areas of the bronchial passage needing treatment. Even if these alternative methods were used, there would still be the possibility of kinking when excessive pressure is applied, whereas arc welding provides more strength in the joint. Arc welding also provides a quicker and easier means of joining the iridium wire and stainless steel wire.

Figure 15:
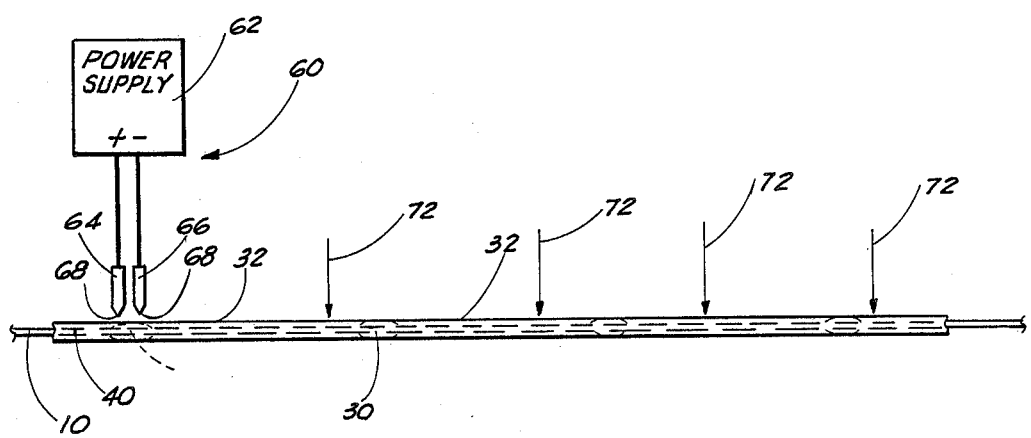
FIG. 15 represents an overall view of the arc welding step in the process of the present invention.

FIG. 15 represents the improvement in the process over what had been disclosed and claimed previously in the pending applications. What is provided is guidewire sheath 32 housing interior inner steel wire 30 joined to IR-192 wire 10. The juncture of IR-192 wire 10 and inner stainless steel wire 30 into sheath 32 fused together to form component 45 is illustrated in FIG. 14. However, one of the other short comings in the former process was the fact that although the fusing as seen in FIG. 14 was accomplished and solved the problem of kinking at the juncture of IR-192 wire 10 and stainless steel wire 30 and sheath 32, there was still presented the problem of the length of the guidewire 30 within sheath 32 posterior to the juncture 40, that would result in kinking since it was not strengthened at those points posterior to the juncture 40. Therefore, in FIG. 15 there is illustrated a length of sheath 32 housing stainless steel wire 30 at that point posterior to juncture 40. In order to assure that kinking will not occur along the length of the guidewire 32, there is illustrated arc welding means 60 which comprises an electrical power supply 62, a pair of electrode-clips 64 and 66, of the type which are commonly known in the arc welding art. The electrode 64 and 66 would further comprise a pair of electrode points 68 which would be used to undertake the arc welding process. As seen in the drawing, points 68 would be placed on the outer layer of sheath 32 and the power supply would then feed electrical current into electrodes 64 and 66. At that point, an arc weld would occur at point 70 in the juncture and would fuse the outer sheath 32 to the inner guidewire 30 at strategic points along the wire indicated by Arrow 72. Although the arc welding had been utilized in the process in order to fuse the stainless steel wire 30 to IR-192 wire 10, this improvement in the process wherein arc welding is utilized to fuse the sheath 32 to the stainless steel wire 30 in order to prevent further kinking posterior to juncture 40 is novel in the process, and offers a vast improvement in the success of the insertion of implant 10 into those areas of the body which are difficult to maneuver the implant therein.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An apparatus for maneuvering a radioactive implant through a human body, the apparatus comprising:
   (a) a guide member;
   (b) a radioactive implant; and
   (c) a wire member,
   wherein the implant is positioned in the guide member, the wire member is secured to the implant, and the guide member is secured to the wire member and the implant adjacent the juncture of the implant and the wire member, and the guide member is secured to the wire member at a plurality of points not adjacent the juncture of the wire member and the implant.

2. The apparatus of claim 1, wherein the wire member is substantially equal in diameter to the implant.

3. The apparatus of claim 1, wherein the implant comprises a core member comprising radioactive iridium, the core member being encased in a platinum sheath.

4. A method of securing a radioactive implant to a guide member to assure successful maneuvering of the implant through a human body, the process comprising the following steps:
   (a) securing a wire member to an end of a radioactive implant;
   (b) inserting the implant and the wire member into a guide member to a point so that the juncture between the implant and the wire member is surrounded by the guide member;
   (c) bonding the guide member to the implant and the wire member adjacent the juncture of the implant and the wire member; and
   (d) arc welding the guide member to the wire member at a plurality of points not adjacent the juncture of the implant and the wire member.

5. The method of claim 4, wherein the implant comprises a core member encased in a platinum sheath, the core member comprising radioactive iridium.

6. The method of claim 4, wherein the wire member comprises stainless steel.

7. The method of claim 4, wherein step (a) comprises arc welding.

8. The method of claim 4, further comprising the step of applying a bonding compound at the juncture of the implant and the wire member prior to inserting the implant and the wire member into the guide member.

9. The method of claim 8, wherein the bonding compound comprises cyanoacrylate ester and the bonding in step (c) is achieved by the use of cyanoacrylate ester.

10. The method of claim 4, wherein the implant has a 0.1 mm iridium/platinum core and a 0.15 mm thick platinum sheath having an end thickness of 0.075 mm.

11. The method of claim 4, wherein the wire member and the implant are substantially equal in diameter.

12. The method of claim 4, further comprising the step of removing a non-penetrable coating from the exterior of the guide member adjacent the juncture of the implant and the wire member prior to performing step (c).

13. A method of preparing and implanting a radioactive implant into a human body, the method comprising the steps of:
   (a) securing a wire member to an end of a radioactive implant;
   (b) positioning the implant and wire member within a flexible guide member;
   (c) bonding the guide member to the implant and the wire member adjacent the juncture of the implant and the wire member;
   (d) arc welding the guide member to the wire member at a plurality of points not adjacent the juncture of the implant and the wire member; and
   (e) maneuvering the guide member within a catheter means to an area of a human body.

14. The method of claim 13, wherein the implant comprises a radioactive core and a non-radioactive sheath encasing the core.

15. The method of claim 14, wherein the radioactive core comprises iridium and the non-radioactive sheath comprises platinum.

16. The method of claim 13, wherein the step of securing the wire member to the implant comprises an arc welding process.

17. The method of claim 13, further comprising the step of applying a bonding compound at the juncture of the implant and the wire member prior to the introduction of the wire member and the implant into the flexible guide member.

18. The method of claim 13, wherein:
the flexible guide member comprises a tightly wound wire and has flow spaces so that a bonding compound applied to the exterior of the guide member can penetrate the guide member for achieving a bond between the guide member and the implant and the wire member, and step (c) comprises applying a bonding compound to the exterior of the guide member.

19. The method of claim 18, wherein the bonding compound comprises cyanoacrylate ester.

20. The method of claim 18, further comprising the step of removal of an exterior, non-penetrable layer on the guide member prior to the application of the bonding compound thereto.

* * * * *